United States Patent
Hecht et al.

(10) Patent No.: US 10,405,790 B2
(45) Date of Patent: Sep. 10, 2019

(54) REVERSE CORRELATION OF PHYSIOLOGICAL OUTCOMES

(71) Applicant: International Business Machines Corporation, Armonk, NY (US)

(72) Inventors: Jae-Lyn Hecht, Boston, MA (US); Fang Lu, Billerica, MA (US); Azadeh Salehi, Pepperell, MA (US); Olga M. Sanchez Sanchez, Littleton, MA (US); Zi C. Sardone, Chelmsford, MA (US)

(73) Assignee: International Business Machines Corporation, Armonk, NY (US)

( * ) Notice: Subject to any disclaimer, the term of this patent is extended or adjusted under 35 U.S.C. 154(b) by 828 days.

(21) Appl. No.: 14/945,667

(22) Filed: Nov. 19, 2015

(65) Prior Publication Data
US 2017/0147578 A1    May 25, 2017

(51) Int. Cl.
*G06F 17/30* (2006.01)
*A61B 5/00* (2006.01)
*A61B 5/048* (2006.01)
*A61B 5/055* (2006.01)
*A61B 5/16* (2006.01)
(Continued)

(52) U.S. Cl.
CPC ............ *A61B 5/4064* (2013.01); *A61B 5/048* (2013.01); *A61B 5/055* (2013.01); *A61B 5/168* (2013.01); *A61B 5/6814* (2013.01); *A61B 5/7264* (2013.01); *G06F 16/903* (2019.01);
(Continued)

(58) Field of Classification Search
CPC ....... A61B 5/4064; A61B 5/048; A61B 5/055; A61B 5/168; A61B 5/6814; A61B 5/7264; A61B 5/04012; A61B 5/7221; A61B 2503/12; G06F 17/30964; G06F 16/903
See application file for complete search history.

(56) References Cited

U.S. PATENT DOCUMENTS

| | | |
|---|---|---|
| 4,454,886 A | 6/1984 | Lee |
| 5,038,782 A | 8/1991 | Gevins et al. |

(Continued)

FOREIGN PATENT DOCUMENTS

WO    2014071556 A1    5/2014

OTHER PUBLICATIONS

James Brewer et al., "Making Memories: Brain Activity that Predicts How Well Visual Experience Will Be Remembered", Aug. 21, 1998, vol. 281, pp. 1185-1187 (Year: 1998).*

(Continued)

*Primary Examiner* — Jared M Bibbee
(74) *Attorney, Agent, or Firm* — Stephen R. Yoder (57) ABSTRACT

Embodiments of the present invention provide systems and methods for performing analysis validity ranking of information. The method utilizes technology such as MRI, CT, PET, SPECT, EEG, and MEG to collect a user's cognitive event, to analyze the user's cognitive event via analytics, and to correlate the user's cognitive event with a ranking. This correlated data is sent to a database amenable to future inquiries on cognitive events of the user. The search results are based on the level of validity for retrieving accurate search results from the database at a future point in time. A validity and the rank of the data deriving from the user's cognitive event are evaluated based on the brainwaves and the location of the data deriving from the user's cognitive event. The data with a higher validity is ranked higher and tagged accordingly.

19 Claims, 2 Drawing Sheets

(51) Int. Cl.
  *G06F 16/903* (2019.01)
  *A61B 5/04* (2006.01)
(52) U.S. Cl.
  CPC ......... *A61B 5/04012* (2013.01); *A61B 5/7221* (2013.01); *A61B 2503/12* (2013.01)

(56) References Cited

U.S. PATENT DOCUMENTS

| | | | |
|---|---|---|---|
| 5,564,433 A * | 10/1996 | Thornton | A61B 5/0476 600/390 |
| 6,052,619 A | 4/2000 | John | |
| 6,067,523 A * | 5/2000 | Bair | G06Q 50/22 705/3 |
| 6,175,762 B1 | 1/2001 | Kirkup et al. | |
| 9,778,351 B1 * | 10/2017 | Khosla | G01S 13/867 |
| 10,009,644 B2 * | 6/2018 | Aimone | H04N 21/42201 |
| 2003/0109797 A1 * | 6/2003 | Kim | A61B 5/0482 600/545 |
| 2004/0096896 A1 * | 5/2004 | Agus | G01N 33/6803 435/7.1 |
| 2005/0228236 A1 | 10/2005 | Diederich et al. | |
| 2006/0004891 A1 | 1/2006 | Hurst-Hiller et al. | |
| 2009/0209845 A1 * | 8/2009 | Christen | A61B 5/0482 600/411 |
| 2010/0023349 A1 * | 1/2010 | Heidel | G06Q 10/10 705/3 |
| 2011/0004115 A1 * | 1/2011 | Shahaf | A61B 5/04009 600/544 |
| 2011/0055131 A1 | 3/2011 | Chen | |
| 2013/0063550 A1 | 3/2013 | Ritchey et al. | |
| 2014/0096035 A1 | 4/2014 | Hall et al. | |
| 2014/0108328 A1 | 4/2014 | Davis | |
| 2014/0223462 A1 * | 8/2014 | Aimone | H04N 21/42201 725/10 |
| 2014/0289172 A1 * | 9/2014 | Rothman | G06N 5/04 706/11 |
| 2015/0026195 A1 * | 1/2015 | Hasegawa | A61B 5/0476 707/748 |
| 2017/0109437 A1 * | 4/2017 | Kudo | G06F 16/35 |

OTHER PUBLICATIONS

Agarwal et al., "Classification of mental tasks from EEG data using backtracking search optimization based neural classifier", Neurocomputing 166, Available online Apr. 3, 2015, pp. 397-403.

Lorist et al., "The influence of mental fatigue and motivation on neural network dynamics; an EEG coherence study." May 13, 2009, 2 pages, <http://www.ncbi.nlm.nih.gov/pubmed/19306850>.

PT Staff, "How Memory Makes Waves", Psychology Today, published on Sep. 1, 1995—last reviewed on Jun. 19, 2012, 2 pages, <https://www.psychologytoday.com/articles/199509/how-memory-makes-waves>.

Rocha et al., "Neural circuits for Motivation", Jan. 5, 2015, pp. 1-34.

Trafton, "How brain waves guide memory formation", MIT News, Feb. 23, 2015, 3 pages, <news.mit.edu/2015/brain-waves-guide-memory-formation-0223>.

"Meet Your Brain Waves—Introducing Alpha, Beta, Theta, Delta, And Gamma", FinerMinds, Printed Aug. 28, 2015, 11 pages, <http://www.finerminds.com/mind-power/brain-waves/>.

"Ranking Search Results Returned from Multiple Search Engines based on a Semantic Model", An IP.com Prior Art Database Technical Disclosure, IP.com No. 000216636, Apr. 11, 2012, pp. 1-6.

"A System and Method of Automatically Rank on Search Result based on User Active Time and User Profile", An IP.com Prior Art Database Technical Disclosure, IP.com No. 000220103, Jul. 23, 2012, pp. 1-6.

"What are Brainwaves?", brainworks, Printed Aug. 28, 2015, 4 pages, <http://www.brainworksneurotherapy.com/what-are-brainwaves>.

* cited by examiner

REVERSE CORRELATION OF PHYSIOLOGICAL OUTCOMES

BACKGROUND OF THE INVENTION

The present invention relates generally to the field of psychology and more specifically to performing analysis validity ranking of information.

It is typical to forget things from time to time. People become more forgetful with increasing age. Healthy people can experience memory loss or memory distortion at any age. Stress, fatigue, insomnia, and sleep deprivation may lead to memory issues. When people are not in their best mental or physical states, the information that gets stored or retrieved in the brain may not be the most accurate information.

SUMMARY

According to one embodiment of the present invention, a method for performing analysis validity ranking of information is provided, the method comprising the steps of: receiving, by one or more processors, information deriving from neural inputs; analyzing, by one or more processors, the information deriving from the neural inputs, wherein the information deriving from the neural inputs is ranked; storing, by one or more processors, the ranked information deriving from the neural inputs in a database; and retrieving, by one or more processors, the ranked information deriving from the neural inputs in the database, upon receiving one or more inquiries from a user.

Another embodiment of the present invention provides a computer program product for performing analysis validity ranking of information, based on the method described above.

Another embodiment of the present invention provides a computer system for performing analysis validity ranking of information, based on the method described above.

DETAILED DESCRIPTION

As neurons emit an action potential, brain waves are produced which oscillate at different frequencies. Two brain regions key to learning in humans—the hippocampus and the prefrontal cortex—use two different brain wave frequencies to communicate as the brain learns to associate unrelated objects. When the brain correctly links the objects, the brain waves oscillate at a higher wave frequency, called "beta" waves. When the brain incorrectly links the objects, the waves oscillate at a lower frequency, called "theta" waves. Within the hippocampus and prefrontal cortex, a correct guess (i.e., a response a user has perceived confidence in, where affiliated neural linkages and pathways are quickly identified and related neuronal firing occurs) generates waves oscillating in the beta frequency (of 9 to 16 hertz or cycles per second). Within the hippocampus and prefrontal context, an incorrect guess generates waves oscillating in the theta frequency (of 2 to 6 hertz). Additional determinants in memory formation and cognitive functioning include the role of different directions of the flow of brain waves; the source of the sending information; the destination of the sent information; the frequency of waves during particular cognitive and memory functioning events. Embodiments of the present invention provide methods and systems to utilize techniques such as Magnetic Resonance Imaging (MRI), computerized axial tomography (CT), positron emission tomography (PET), single-photo emission computed tomography (SPECT), electroencephalogram (EEG), and magnetoencephalogram (MEG) to collect, analyze and label a user's memory data based on the validity into a question and answer (Q&A) system for retrieving accurate search results at a future point. The validity and rank of the data is evaluated based on the brain waves and location of the data in the user's memory. The data with higher validity is ranked higher and tagged accordingly in the Q&A system.

Figure 1:
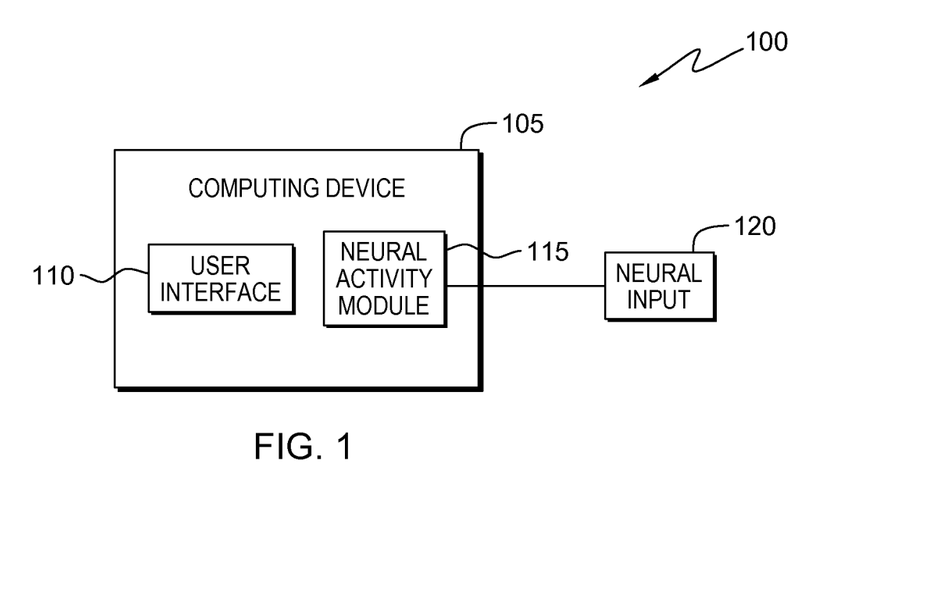
FIG. 1 is a functional block diagram illustrating a data processing environment, in accordance with an embodiment of the present invention.

The present invention will now be described in detail with reference to the Figures. FIG. 1 is a functional block diagram illustrating a data processing environment, generally designated 100, in accordance with one embodiment of the present invention. FIG. 1 provides only an illustration of implementation and does not imply any limitations with regard to the environments in which different embodiments may be implemented. Modifications to data processing environment 100 may be made by those skilled in the art without departing from the scope of the invention as recited by the claims. In this exemplary embodiment, data processing environment 100 includes neural input 120 and computing device 105.

Neural input 120 refer to sources of data deriving from the brain/neural activity of a user. Neural input 120 sends the brain/neural activity of the user and is connected directly to a sensor which resides and/or works in conjunction with neural activity module 115. In one embodiment, a brain wave detecting system is located within a flexible hat which is placed on the head of the user. The flexible hat contains a plurality of electrodes conforming to the hat. A circuit board having a low-noise integrated circuit amplifier may be mounted thereon. Each electrode uses a plurality of metal conductive fingers which protrude through the hair to the scalp of the user and provide multi-contact sites on the scalp for each electrode. The tips of each electrode contact the user's scalp to provide a redundancy of contacts for each electrode.

Computing device 105 comprises of neural activity module 115 and user interface 110. Computing device 105 may be a laptop computer, a tablet computer, a netbook computer, a personal computer (PC), a desktop computer, a personal digital assistant (PDA), a smart phone, a thin client, or any programmable electronic device capable of communicating with neural input 120. Computing device 105 may include internal and external hardware components, as depicted and described in further detail with respect to FIG. 3.

User interface 110 may be a graphical user interface (GUI) or a web user interface (WUI) and can display text, documents, web browser windows, user options, application interfaces, and instructions for operation, and includes the information (such as graphics, text, and sound) a program presents to a user and the control sequences the user employs to control the program. User interface 110 is capable of receiving data, user commands, and data input modifications from a user. User interface 110 is also capable of communicating with neural activity module 115.

In this exemplary embodiment, neural activity module 115 is an application capable of reading, consuming, and manipulating data deriving from neural inputs 120. Neural activity module 115 comprises of at least: (i) a set of processors; (ii) a memory coupled to at least one of the processors; (iii) a set of sensors for capturing indications of neural activity of a user; (iv) a set of receivers for receiving the indications of neural activity of the user; (v) a set of instructions stored in the memory and executed by at least one of the set of processors, wherein the set of instructions perform the actions of: (a) receiving indications of the neural activity of the user associated with an interactive flow of information communicated between the user and the system, (b) identifying a user cognitive state from the neural activity to form a ranked accuracy assessment of a data derived from a statement input by the user; and (c) storing and associating the data (e.g., by tagging) and the ranked accuracy assessment of the data in a memory repository for subsequent usage based on the ranked accuracy assessment. Furthermore, sensors and/or receivers perform the following functionalities: (i) application of an EEG scan to identify a brain wavelength associated with the cognitive event; and (ii) application of a MRI scan to identify neural patterns. Neural activity module 115 applies a neural state assessment algorithm which associate a cognitive assessment based on the brain wavelength; and applies a neural pattern to associate a memory retrieval accuracy to a cognitive event. Neural activity module 115 provides a validity ranking of information from a user based on detected neural activity of the user and is capable of answering questions asked by a user via data based on the ranking to answer questions.

Alpha, beta, theta, delta, and gamma waves can correspond to neural activity.

Alpha waves (e.g., the deep relaxation waves) oscillate between 7.5 Hz and 14 Hz. Alpha brain waves are present in deep relaxation, typically when the eyes are closed, and times of slipping into a daydream or during light meditation. Alpha waves are associated with an optimal time to program the mind for success and it also heightens an individual's level of imagination, visualization, memory, learning and concentration. Alpha waves are the gateway to a subconscious mind; lies at the base of conscious awareness; and is present in an individual's intuition (which becomes clearer and more profound as a brain wave approaches 7.5 Hz).

Beta waves (e.g., the waking consciousness and reasoning waves) oscillate between 14 Hz and 40 Hz. Beta brain waves are associated with normal waking consciousness; a heightened state of alertness; moments requiring logic and critical reasoning; and moments characterized with stress, anxiety, and restlessness. Beta brain waves dominate an individual's normal waking state of consciousness when attention is directed towards cognitive tasks and involves activity present when individuals are alert, attentive, engaged in problem solving, judgment, decision making, and engaged in focused mental activity.

Theta waves (e.g., the light meditation and sleeping wave) oscillate between 4 Hz and 7.5 Hz. Theta brain waves are present during deep meditation, light sleep, and a REM dream state. Theta waves are the realm of sub-consciousness and are only experienced momentarily from drifting off to sleep (from alpha waves) and waking from deep sleep (from delta waves). A sense of deep spiritual connection and unity with the universe can be experienced at theta waves wherein a mind's most deep-seated programs are at theta wave frequencies. Thus, individuals experience vivid visualizations, great inspirations, profound creativity and exceptional insights. Unlike other brain waves, the elusive voice of theta waves is a silent voice. At the alpha wave-theta wave border (from 7 Hz to 8 Hz) is where the optimal range for visualization, mind programming, and using the creative power of the brain begins. The alpha wave-theta wave is the mental state which an individual can consciously create a reality. At the frequency from 7 Hz to 8 Hz, individuals are conscious of their surroundings, however the individual's body is in deep relaxation.

Delta waves (e.g., the deep sleep wave) oscillate between 0.5 Hz and 4.0 Hz. The delta wave frequency is the slowest of the frequencies and is experienced in deep, dreamless sleep and in very deep, transcendental meditation where awareness is fully detached. Delta waves are in the realm of an unconscious mind, and is a gateway to the universal mind and the collective unconscious (where information received is otherwise unavailable at the conscious level). Among many things, deep sleep is important for the healing process linked with deep healing and regeneration. Thus, not having enough deep sleep is detrimental to an individual's health in multiple ways.

Gamma waves (e.g., the insight wave) oscillates above 40 Hz (which is the fastest known frequency). Gamma waves are associated with bursts of insight and high-level information processing cycles.

Long-term memories are based on the patterns of connections between neurons. Cells utilize electrical signals to keep track of short-term memories. As long as cells retain a memory, the cells fire in cycles, or oscillations which last between 20 and 40 milliseconds. At this point, time-sharing is invoked. Human brains also produce longer electrical signals—alpha and theta waves—which last about 200 milliseconds. Seven of the 20-to-40-millisecond cycles can be fitted into slots by dividing long waves (i.e., higher wavelengths) into slots. Each memory takes its place in a designated slot of the longer brain waves. Computer simulations confirm that a neural network operating under these conditions can (with appropriate input and feedback) store about seven memories. Subjects took about four-tenths of a second to answer plus a delay of 38 milliseconds for each item on the list. The delay indicates how long it takes to scan through each short-term memory (which corresponds to the 20 to 40 millisecond storage cycles).

Mental fatigue and motivation influences neural network dynamics activated during task switching. EEG coherence is used as a measure of synchronization of brain activity. Electrodes of interest are identified using a data-driven pre-processing method with data-driven visualization and group analysis of multichannel EEG coherence with functional units. Performance on repetition trials are faster and more accurate than on switch trials. EEG data revealed more pronounced and frequency specific frontal-parietal network activation in switch trials, while power density was higher in repetition trials. The effects of mental fatigue on power and coherence are widespread, and are not limited to specific frequency bands. Moreover, these effects are independent of specific task manipulations. This increase in neuronal activity and stronger synchronization between neural networks did not result in more efficient performance. Response speed decreased and the number of errors increases in fatigued subjects. The dopamine system is a proposed as the operable mechanism for the observed the fatigue effects. Brain activity (investigated by EEG scans) can be associated with reasoning required to identify necessities for achieving and maintaining desired goals and with motivation to act with such an intention. Three different components brain activity provide distinct neural signatures for each scene analysis and comprehension which demonstrates that motivation is a very complex psychological concept supported by a widely distributed neural processing.

Figure 2:
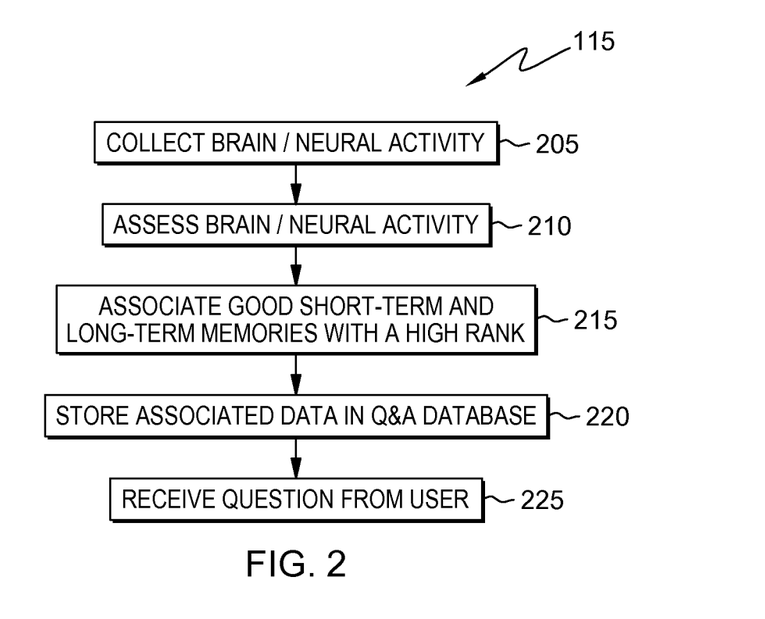
FIG. 2 is a flowchart depicting the processing steps carried out by neural activity module 115, in accordance with an embodiment of the present invention.

FIG. 2 is a flowchart depicting the processing steps carried out by neural activity module 115, in accordance with an embodiment of the present invention.

In step 205, neural activity module 115 collects brain/neural activity. The brain/neural activity is typically in the form of brain waves and memories. A working memory is the equivalent of short term memory while a reference memory is the equivalent of long term memory. Different states of consciousness have various referral output memories such as chemical and physiological expressions. Techniques such as MRI, CT, PET, SPECT, EEG, MEG are used to collect brain/neural activity. In other embodiments, devices which are used to investigate neural particles and affiliated pathways; energy transference; and gravimetric techniques can be used to collect brain/neural activity. The brain/neural activity is treated as the user's memory data which is to be processed at later steps. Neural activity module 115 can collect statistical data for further analysis.

In step 210, neural activity module 115 assesses brain/neural activity. Through existing data stored in a memory repository, neural activity module 115 determines the reverse correlation of good working and reference memories and the relayed outcomes inclusive of physiological effects and neural patterns. Neural activity module 115 triggers the expressions of these cellular networks and assigns the good working memory and reference memory based on the frequency of waves. Techniques such as EEG and MRI are implemented to collect the data (i.e. extract information) from the output memory. EEG scans determine the wavelength and MRI scans determine the magnetic activities and localization of the neuronal patterns. By utilizing existing neuroimaging and cognitive applications, the reverse correlation between specific wavelength patterns (alpha, delta and gamma, especially beta and theta waves) cross-referenced with the MRI locational data determine which wavelength patterns leads to a good working and reference memory. By applying a neural state assessment algorithm, a cognitive assessment is associated with a neural frequency. For example, if an individual has the same frequency of beta waves when recalling a clear, accurate memory, neural activity module 115 can try to replicate the external environment inclusive of similar stimuli, methodology and processes. In another embodiment, neural activity module 115 focuses on assessing the psychological or physiological state by analyzing language cues captured from a patient. Neural activity module can determine general patterns and trends in the data deriving from the brain/neural activity and eliminate events deemed to be outliers.

In step 215, neural activity module 115 associates good short-term memories (i.e., working memories) and good long-term memories (i.e., reference memories) with a high rank. A ranking algorithm constructs a rank based on the validity of working memories and reference memories. Once correlational patterns are identified, additional variables such as personality, learning styles, and memory challenges are identified (if configured to do so). From there, improved methodologies for learning can be applied that fits the needs of the individual. For example, if an individual's personality falls within a category of the Myers Briggs Test and there is a level of bias in the self-questionnaire, then the physiological output comparison can be cross-referenced to support the test or the degree of variance. Neural activity module 115 tags the data which is associated with the good working and reference memory with a higher rank. Conversely, the data which is not associated with a good working or good reference memory is tagged with a lower rank. A ranked accuracy is assessed on data derived from statements received by neural activity module 115. If an individual's homeostatic baseline can be found, neural activity module 115 assesses memory stability and retention potential.

In step 220, neural activity module 115 stores the associated data in a Q&A database. By storing and associating the data (e.g., tagging), the ranked accuracy assessment of the data in the system is available for future usage. The Q&A database is configured to receive requests from users to find the associated data comprising of good working and reference memories with ranks.

In step 225, neural activity module 115 receives a question from the user. Neural activity module 115 retrieves the data from the Q&A database based on the validity rank. Search results are displayed, with the data with the most valid search data on the top of the rank (i.e., the data from the Q&A database which is most relevant to the inquiry in the question from the user). An example of neural activity module 115 receiving a question and retrieving data from the Q&A database includes: (i) receiving a sample question of "What are the best information the new hires got from 5 weeks long bootcamp training and how well they have retained the information?"; (ii) retrieving a resting neurowave frequency (e.g., state of mind); (iii) identifying the difference from that homeostatic state to one of a positive correlation with beta waves which suggests the potential for a good point of working and reference memory; (iv) identifying retained memory data based on spatial data and the user's output of recollection; (v) retrieving related information entered in by the new hire associated with a positive attribute; (vi) identifying the positive attribute which is associated with a higher validity rank; (vii) retrieving related information entered in by the new hire associated with a negative attribute; (viii) identifying the negative attribute which is associated with a lower validity rank; and (ix) outputting the search results to the user. An algorithm within neural activity module evaluates the data based on brainwaves and the location of the data in the user memory in order to derive the rank of the data based on the validity of a stored cognitive event with the search inquiry. The level of validity is assessed by a user confidence level (e.g., perceived cognitive accuracy, biometric correlations, especially focusing on neural frequencies, and other state determinants).

Neural activity module 115 can be applied in different scenarios. Additional applications include: employee engagement, assessment of periods of times of peak efficiency (i.e., when memory and alertness of an individual is at its highest level). Thus, a workforce approach can be applied to identify working environments which are a best fit for an individual. Further enhanced applications may include increased diagnostic and treatment speed and accuracy of neurodegenerative diseases related to memory such as dementia, Alzheimer's disease, aphasias and trauma. A similar analogy can be applied to children learning styles. If the children are stressed and tired, then the data is deemed as less valid in comparison to the data entered when the children are in good mood and alert. Neural activity module 115 detects that evidence/data and tags the data accordingly.

Figure 3:
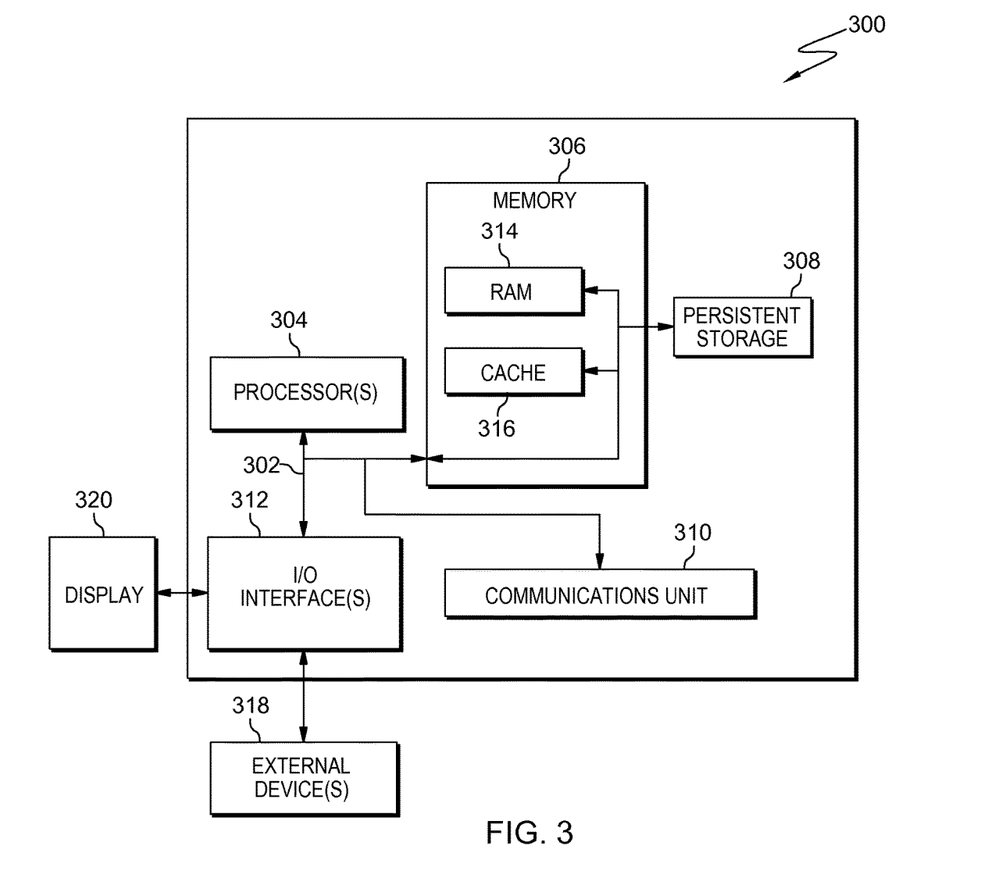
FIG. 3 depicts a block diagram of components of a computing device, in accordance with an illustrative embodiment of the present invention.

FIG. 3 depicts a block diagram of components of a computing device, generally designated 300, in accordance with an illustrative embodiment of the present invention. It should be appreciated that FIG. 3 provides only an illustration of one implementation and does not imply any limitations with regard to the environments in which different embodiments may be implemented. Many modifications to the depicted environment may be made.

Computing device 300 includes communications fabric 302, which provides communications between computer processor(s) 304, memory 306, persistent storage 308, communications unit 310, and input/output (I/O) interface(s) 312. Communications fabric 302 can be implemented with any architecture designed for passing data and/or control information between processors (such as microprocessors, communications and network processors, etc.), system memory, peripheral devices, and any other hardware components within a system. For example, communications fabric 302 can be implemented with one or more buses.

Memory 306 and persistent storage 308 are computer readable storage media. In this embodiment, memory 306 includes random access memory (RAM) 314 and cache memory 316. In general, memory 306 can include any suitable volatile or non-volatile computer readable storage media.

Program instructions and data used to practice embodiments of the present invention may be stored in persistent storage 308 for execution and/or access by one or more of the respective computer processors 304 via one or more memories of memory 306. In this embodiment, persistent storage 308 includes a magnetic hard disk drive. Alternatively, or in addition to a magnetic hard disk drive, persistent storage 308 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 310, in these examples, provides for communications with other data processing systems or devices. In these examples, communications unit 310 includes one or more network interface cards. Communications unit 310 may provide communications through the use of either or both physical and wireless communications links. Program instructions and data used to practice embodiments of the present invention may be downloaded to persistent storage 308 through communications unit 310.

I/O interface(s) 312 allows for input and output of data with other devices that may be connected to computing device 300. For example, I/O interface 312 may provide a connection to external devices 318 such as a keyboard, keypad, a touch screen, and/or some other suitable input device. External devices 318 can also include portable computer readable storage media such as, for example, thumb drives, portable optical or magnetic disks, and memory cards. Software and data used to practice embodiments of the present invention, e.g., software and data, can be stored on such portable computer readable storage media and can be loaded onto persistent storage 308 via I/O interface(s) 312. I/O interface(s) 312 also connect to a display 320.

Display 320 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience and thus, the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method comprising the steps of:
    monitoring neural activity of a user while the user performs a memory functioning event via a user interface on a device;
    recording the memory functioning event as a set of individual memories;
    capturing the neural activity from neural inputs, the neural activity including brain wave information;
    associating an individual memory of the memory functioning event with a corresponding neural activity at the time of the individual memory;
    assigning to the individual memory a wave type based on the brain wave information of the corresponding neural activity, the wave type being assigned from among a set of wave types including beta waves and theta waves;
    ranking, with a first rank, the individual memory according to the assigned wave type, the beta waves being ranked higher than the theta waves;
    tagging the individual memory with the first rank;
    storing the ranked and tagged individual memory in a database; and
    retrieving the ranked and tagged individual memory, based on the tag and upon receiving one or more inquiries from the user.

2. The method of claim 1, wherein capturing the neural activity from neural inputs, comprises:
    collecting brain wave activity by, at least, a magnetic resonance imaging (MRI) scan and an electroencephalogram (EEG) scan, wherein the EEG scan identifies a brain wave frequency associated with the memory functioning event and the MRI scan identifies a localization of neural patterns during the memory functioning event; and
    receiving, by one or more processors, the collected brain wave activity for further processing.

3. The method of claim 2, wherein assigning the wave type, comprises:
    measuring a frequency of the brain wave while monitoring the neural activity, the brain wave information including a frequency measurement;
    determining brain wave location information from the localization of neural patterns, the brain wave information including the brain wave location information;
    correlating the frequency measurement and the brain wave location information, with the memory functioning event; and
    associating the brain wave information with the memory functioning event.

4. The method of claim 3, further comprising:
    constructing the database, wherein the database stores the brain wave information inputs and the brain wave location information deriving from the neural inputs, with the memory functioning event;
    corresponding a validity value to the memory functioning event wherein the validity value is a first validity level for a first attribute and a second validity level for a second attribute; and
    utilizing the database for a search inquiry for a valid memory, wherein the valid memory has a high rank relative to other related memories in the database.

5. The method of claim 4, wherein the validity value comprises at least two memory functioning events, and wherein the at least two memory functioning events are ranked based on their associated attributes.

6. The method of claim 4, further comprising:
responsive to the search inquiry, outputting search results as a list with the brain wave information and corresponding memory functioning event based on the validity.

7. A computer program product comprising:
a computer readable storage medium and program instructions stored on the computer readable storage medium, the program instructions comprising:
program instructions to monitor neural activity of a user while the user performs a memory functioning event via a user interface on a device;
program instructions to record the memory functioning event as a set of individual memories;
program instructions to capture the neural activity from neural inputs, the neural activity including brain wave information;
program instructions to associate an individual memory of the memory functioning event with a corresponding neural activity at the time of the individual memory;
program instructions to assign to the individual memory a wave type based on the brain wave information of the corresponding neural activity, the wave type being assigned from among a set of wave types including beta waves and theta waves;
program instructions to rank, with a first rank, the individual memory according to the assigned wave type, the beta waves being ranked higher than the theta waves;
program instructions to tag the individual memory with the first rank;
program instructions to store the ranked and tagged individual memory in a database; and
program instructions to retrieve the ranked and tagged individual memory, based on the tag associated with the information and upon receiving one or more inquiries from the user.

8. The computer program product of claim 7, wherein program instructions to capture the neural activity from neural inputs comprise:
program instructions to collect brain wave activity by, at least, a magnetic resonance imaging (MRI) scan and an electroencephalogram (EEG) scan, wherein the EEG scan identifies a wave frequency associated with the memory functioning event and the MRI scan identifies a localization of neural patterns during the memory functioning event; and
program instructions to receive the collected brain wave activity for further processing.

9. The computer program product of claim 8, wherein program instructions to assign the wave type comprise:
program instructions to measure a frequency of the brain wave while monitoring the neural activity, the brain wave information including a frequency measurement;
program instructions to determine brain wave location information from the localization of neural patterns, the brain wave information including the brain wave location information;
program instructions to correlate the frequency measurement and the brain wave location information, with the memory functioning event; and
program instructions to associate the brain wave information with the memory functioning event.

10. The computer program product of claim 9, further comprising:
program instructions to construct the database, wherein the database stores the brain wave information inputs and the brain wave location information deriving from the neural inputs, with the memory functioning event;
program instructions to correspond a validity value to the memory functioning event wherein the validity value is a first validity level for a first attribute and a second validity level for a second attribute; and
program instructions to utilize the database for a search inquiry for a valid memory, wherein the valid memory has a high rank relative to other related memories in the database.

11. The computer program product of claim 10, wherein the validity value comprises at least two memory functioning events, and wherein the at least two memory functioning events are ranked based on their associated attributes.

12. The computer program product of claim 10, further comprises:
program instructions to, responsive to the search inquiry, output search results as a list with the brain wave information and corresponding memory functioning event based on the validity.

13. A computer system comprising:
one or more computer processors;
one or more computer readable storage media; and
program instructions stored on the one or more computer readable storage media for execution by at least one of the one or more processors, the program instructions comprising:
program instructions to monitor neural activity of a user while the user performs a memory functioning event via a user interface on a device;
program instructions to record the memory functioning event as a set of individual memories;
program instructions to capture the neural activity from neural inputs, the neural activity including brain wave information;
program instructions to associate an individual memory of the memory functioning event with a corresponding neural activity at the time of the individual memory;
program instructions to assign to the individual memory a wave type based on the brain wave information of the corresponding neural activity, the wave type being assigned from among a set of wave types including beta waves and theta waves;
program instructions to rank, with a first rank, the individual memory according to the assigned wave type, the beta waves being ranked higher than the theta waves;
program instructions to tag the individual memory with the first rank;
program instructions to store the ranked and tagged individual memory in a database; and
program instructions to retrieve the ranked and tagged individual memory, based on the tag and upon receiving one or more inquiries from the user.

14. The computer system of claim 13, wherein program instructions to capture the neural activity from neural inputs comprise:
program instructions to collect brain wave activity by, at least, a magnetic resonance imaging (MRI) scan and an electroencephalogram (EEG) scan, wherein the EEG scan identifies a wave frequency associated with the memory functioning event and the MRI scan identifies a localization of neural patterns during the memory functioning event; and
program instructions to receive the collected brain wave activity for further processing.

15. The computer system of claim 14, wherein program instructions to assign the wave type comprise:
  program instructions to measure a frequency of the brain wave while monitoring the neural activity, the brain wave information including a frequency measurement;
  program instructions to determine brain wave location information from the localization of neural patterns, the brain wave information including the brain wave location information;
  program instructions to correlate the frequency measurement and the brain wave location information, with the memory functioning event; and
  program instructions to associate the brain wave information with the memory functioning event.

16. The computer system of claim 15, further comprising:
  program instructions to construct the database, wherein the database stores the brain wave information inputs and the brain wave location information deriving from the neural inputs, with the memory functioning event;
  program instructions to correspond a validity value to the memory functioning event wherein the validity value is a first validity level for a first attribute and a second validity level for a second attribute; and
  program instructions to utilize the database for a search inquiry for a valid memory, wherein the valid memory has a high rank relative to other related memories in the database.

17. The computer system of claim 16, wherein the validity value comprises at least two memory functioning events, and wherein the at least two memory functioning events are ranked based on their associated attributes.

18. The computer system of claim 16, further comprising:
  program instructions to, responsive to the search inquiry, output search results as a list with the brain wave information and corresponding memory functioning event based on the validity.

19. The method of claim 1, wherein monitoring neural comprises:
  collecting brain wave activity by energy transference.

* * * * *